United States Patent
Yokoyama et al.

(10) Patent No.: US 7,094,462 B1
(45) Date of Patent: Aug. 22, 2006

(54) BASE MATERIAL FOR WIPING SHEET

(75) Inventors: Machiko Yokoyama, Tochigi-ken (JP); Manabu Kaneda, Tochigi-ken (JP); Takashi Kawai, Tochigi-ken (JP); Yasuhiro Komori, Tochigi-ken (JP); Shoichi Taneichi, Tochigi-ken (JP); Katsuhiko Takeuchi, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/539,791

(22) Filed: Mar. 31, 2000

(30) Foreign Application Priority Data

Apr. 2, 1999 (JP) .......................................... 11-096469
Apr. 2, 1999 (JP) .......................................... 11-096470

(51) Int. Cl.
*B32B 3/26* (2006.01)
*B32B 5/24* (2006.01)
*B32B 3/00* (2006.01)
*B32B 5/16* (2006.01)
*D21H 11/00* (2006.01)
*D21H 13/00* (2006.01)
*D04H 1/00* (2006.01)
*D04H 13/00* (2006.01)
*D04H 1/46* (2006.01)
*D04H 3/10* (2006.01)

(52) U.S. Cl. ............................... 428/304.4; 428/311.11; 428/315.5; 428/315.9; 442/342; 442/393; 442/402; 442/417

(58) Field of Classification Search .................... 428/98, 428/131, 137, 304.11, 311.11, 315.5, 315.9, 428/304.4; 442/342, 393, 402, 417; 604/381
See application file for complete search history.

(56) References Cited

U.S. PATENT DOCUMENTS

| | | | | |
|---|---|---|---|---|
| 4,284,465 A | * | 8/1981 | Walbrun ...................... 428/166 |
| 4,550,035 A | * | 10/1985 | Smith .......................... 427/398 |
| 4,606,958 A | | 8/1986 | Haq et al. |
| 4,683,001 A | * | 7/1987 | Floyd et al. .................... 106/3 |
| 4,690,825 A | * | 9/1987 | Won ............................ 424/501 |
| 4,882,204 A | * | 11/1989 | Tenenbaum ................. 427/180 |
| 4,904,524 A | * | 2/1990 | Yoh .......................... 428/311.3 |
| 5,043,155 A | * | 8/1991 | Puchalski et al. .............. 424/78 |
| 5,137,600 A | | 8/1992 | Barnes et al. |
| 5,328,759 A | * | 7/1994 | McCormack et al. ........ 428/283 |
| 5,350,624 A | * | 9/1994 | Georger et al. ............. 428/219 |
| 5,427,696 A | | 6/1995 | Phan et al. |
| 5,611,890 A | | 3/1997 | Vinson et al. |
| 5,648,083 A | * | 7/1997 | Blieszner et al. ............ 424/402 |
| 5,871,763 A | * | 2/1999 | Luu et al. ................... 424/402 |
| 5,882,638 A | * | 3/1999 | Dodd et al. ................... 424/65 |
| 5,990,377 A | * | 11/1999 | Chen et al. ................. 604/381 |
| 6,054,202 A | * | 4/2000 | Takeuchi et al. ............ 428/167 |
| 6,228,385 B1 | * | 5/2001 | Shick .......................... 424/419 |
| 6,423,329 B1 | * | 7/2002 | Sine et al. ................... 424/405 |

FOREIGN PATENT DOCUMENTS

| | | |
|---|---|---|
| EP | 0 202 472 A1 | 11/1986 |
| EP | 0 950 391 A1 | 10/1999 |
| EP | 0950391 A1 * | 10/1999 |
| JP | 63209621 | 8/1988 |
| JP | 2-036114 | 2/1990 |
| JP | 424480 | 4/1992 |
| JP | 4146257 | 5/1992 |
| JP | 4146300 | 5/1992 |
| JP | 4-281056 A | 10/1992 |
| JP | 7-255630 A | 10/1995 |
| JP | 8-505663 A | 6/1996 |
| JP | 9-217293 A | 8/1997 |
| JP | 11-47026 A | 2/1999 |
| JP | 11-503495 A | 3/1999 |
| JP | 2000-273492 A | 10/2000 |
| WO | WO 9517175 A1 * | 6/1995 |

OTHER PUBLICATIONS

JP–11–503495–A (Laid–Open Date Mar. 26, 1999) Full English Translation.
JP–4–281056–A (Laid–Open Date Oct. 6, 1992) Full English Translation.
JP–8–505663–A (Laid–Open Date Jun. 18, 1996) Full English Translation.

* cited by examiner

*Primary Examiner*—Elizabeth M. Cole
*Assistant Examiner*—Jeremy R. Pierce
(74) *Attorney, Agent, or Firm*—Birch, Stewart, Kolasch & Birch, LLP

(57) ABSTRACT

A base material for a wiping sheet on which powder is to be supported, wherein the ratio of the average pore diameter (D) of the surface of the base material while dry as measured by the mercury penetration method to the average particle diameter (d) of the powder, D/d, ranges from 0.03 to 30, and the base material while dry has a bulk softness of from 0.1 to 5 N/30 mm and a thickness of from 0.3 to 5 mm.

9 Claims, No Drawings

US 7,094,462 B1

BASE MATERIAL FOR WIPING SHEET

BACKGROUND OF THE INVENTION

The present invention relates to a base material for a wiping sheet having powder which is used to wipe an object including the human body, and a wiping sheet comprising the base material having powder supported thereon and/or impregnated with an aqueous medium.

A wiping sheet, such as a wet tissue or a wet wiper, comprises a base sheet, such as woven or nonwoven fabric of rayon or cotton, impregnated with purified water, lotion, an alcohol, etc. and is used as a disposable towel, a facial cleansing sheet, a body wiping sheet for babies or patients, a cleaner for office-automation equipment, a kitchen wiper, and the like. For instance, a good number of wet type personal care goods have been on the market as a wiping sheet for bodies, particularly the face, the neck, hands and feet, etc. These wiping sheets are used for wiping the skin or for giving a refreshment.

Although the conventional wiping goods are effective in wiping the skin, they are liable to remove too much sebum or moisture, which often causes discomfort after use depending on the part of the body. For example, a thorough wipe with a wet tissue given to an armpit sometimes causes skin roughening. While the currently available personal care goods of this type are intended to be applicable to the body, they are not suitable for wiping the whole body everyday, the actual use being confined to the relatively dirty parts, such as hands and feet.

Most of the base materials used in the conventional wiping sheets such as wet tissues and wet wipers are made of cellulosic materials, such as 100% cuprammonium rayon nonwoven, 100% cotton nonwoven, water-needled nonwoven mainly comprising rayon, a wet or dry process pulp sheet, and the like. Since these materials have poor thermal formability due to insusceptibility to heat, they are often supplied as a single ply. Commercially supplied goods include individually packaged sheets, a packet containing 10 to 80 sheets each folded into two or so, and a roll of a perforated continuous sheet. These goods are so simple that they are easy to manufacture, but are not user friendly because they have insufficient thickness for good texture and are easily twisted due to poor nerve (stiffness), which causes discomfort to a user.

Apart from the wet type goods, it is effective to apply powder, such as baby powder, to the wiped skin to keep comfort. Since wiping with a wet tissue followed by powder application is troublesome, a wet tissue having powder thereon is conceivable, with which to wipe the skin and to apply powder simultaneously. In this case, however, the powder would be held in the inside of the base sheet constituting the wet tissue more than on the surface and could not be applied to the skin efficiently, failing to give a sufficient comfort after wiping. Further, where used for wiping an object, a wet tissue having powder is expected to produce surface improving effects attributed to the powder, such as reduction in friction, as well as the cleaning effect. However, the surface improving effects as expected are not obtained for the same reason as in the application to the skin.

SUMMARY OF THE INVENTION

Accordingly, an object of the present invention is to provide a base material for a wiping sheet which is capable of efficiently applying powder supported thereon to the surface to be wiped.

Another object of the present invention is to provide a base material for a wiping sheet which is bulky enough for a user to feel a sufficient thickness, comfortable to wipe with, is not twisted while used, has a soft texture, and has sufficient liquid retention.

The present inventors have found that the above objects are accomplished by defining the ratio of the average pore diameter of the base material while dry to the particle diameter of the powder to be supported and the dry bulk softness and dry thickness of the base material.

The present invention has been completed based on this finding. The present invention provides a base material for a wiping sheet on which powder is to be supported, wherein the ratio of the average port diameter (D) of the surface of said base material while dry as measured by the mercury penetration method to the average particle diameter (d) of said powder, D/d, ranges from 0.03 to 30, and said base material while dry has a bulk softness of from 0.1 to 5 N/30 mm and a thickness of from 0.3 to 5 mm.

The present invention also provides a wiping sheet comprising the above-described base material having powder supported thereon and/or impregnated with an aqueous medium.

DETAILED DESCRIPTION OF THE PREFERRED EMBODIMENTS

The preferred embodiments of the base material for a wiping sheet according to the present invention will be described in detail. The base has a sheet form (hereinafter referred to as a "base sheet") on which powder is to be supported. The average pore diameter (D) of the surface of the base sheet while dry satisfies the relationship with the average particle diameter (d) of the powder to be supported; D/d=0.03 to 30, preferably D/d=0.1 to 15. With this D/d relationship being satisfied, powder can be supported on the surface, or in the vicinity of the surface, of the base sheet more than in the inside and is therefore ready to be transferred to the surface of an object of wiping. A base sheet having the D/d ratio smaller than 0.03, i.e., a sheet whose pore diameter D is far smaller than the average particle diameter d of powder is practically difficult to make and also causes the powder to agglomerate considerably on the sheet surface, resulting in poor texture. If the D/d ratio exceeds 30, the powder enters deep into the sheet and will not be transferred to an object of wiping efficiently.

The average pore diameter D of the base sheet surface is measured by the mercury penetration method. The term "while dry" denotes the condition after the base sheet is allowed to stand at 20° C. and 65% RH for at least 24 hours.

The D/d ratio falling within the above-specified range, it is preferred that the D value (the average pore diameter of the base sheet surface) be in the range of 0.1 to 30 µm, particularly 1 to 20 µm, so that the powder may be effectively prevented from entering into the inside of the base sheet.

The base sheet, while dry, has a bulk softness of from 0.1 to 5 N/30 mm, preferably 0.3 to 3 N/30 mm. The bulk softness within this range secures improved texture of the base sheet. If the bulk softness is less than 0.1 N/30 mm, the texture is too soft to give a user a feel of solidity. If it is more than 5 N/30 mm, the texture is too hard.

The bulk softness is measured as follows. A 150 mm long and 30 mm wide strip is cut out of a base sheet and looped with an overlap of about 10 mm to make a cylinder of 45 mm in diameter with the width of the strip corresponding to the height of the cylinder. The overlap is fixed by stapling or something. The cylinder is compressed vertically at a speed of 10 mm/min, and the maximum buckling stress is measured, which is taken as a bulk softness.

The base sheet, while dry, has a thickness of 0.3 to 5 mm, with which to give a user a feel of solidity. A preferred thickness is from 0.5 to 2 mm. The term "thickness" as used herein means the one measured under a load of 3.7 g/cm$^2$.

It is preferred for the base sheet to have unevenness for improving the bulkiness and the texture. Unevenness can be formed by, for example, embossing using a matched pair of steel embossing rolls each having a large number of bosses arranged regularly (hereinafter "matched steel roll embossing"). In more detail, the bosses of the two rolls are facing to each other in such a manner that projections on one roll match the depressions of the other. The base sheet is pressed between the two rolls to be given the emboss pattern.

The two sides of the base sheet preferably have substantially the same performance in absorbing or releasing liquid, supporting powder, transferring the powder to an object of wiping, and/or wiping off dirt. This is advantageous for making the wiping sheet usable on its both sides with powder supported thereon and/or with liquid impregnating therein.

In case where the base sheet is impregnated with an aqueous medium to make a wiping sheet, a plurality of the wiping sheets are usually stacked and packaged for distribution and storage. If the base sheet does not have sufficient liquid retention, the absorbed aqueous medium gradually moves down, resulting in a difference in content of the liquid between the upper wiping sheets and the lower ones. When the stack of the sheets is used from its top, the wiping sheet will have poor wiping performance due to insufficient wetness. When the stack is used from its bottom, on the other hand, the wiping sheet is so wet that the excess liquid will remain on the object of wiping. Hence, it is desirable for the base sheet to have resistance against such liquid migration. Preferred liquid migration resistance can be quantitatively represented as follows.

Thirty base sheets of 150 mm in length and 100 mm in width are each impregnated with 2.75 times its own weight of an impregnating liquid (hereinafter described) and stacked one on another. After the stack is left to stand for 24 hours, the five base sheets from the top and the five base sheets from the bottom were weighed to obtain an average liquid content (%) of the top five and that of the bottom five. The difference between the two average liquid contents (the former minus the later) (hereinafter referred to as a liquid migration) is taken as a measure of the liquid retention. It is preferred for the base sheet of the present invention to have a liquid migration of 30% or less, particularly 15% or less. As a matter of course, the ideal liquid migration is 0%. It is a prerequisite for making the above-mentioned liquid migration measurement that the liquid content difference between the middle base sheet of the stack and the top or bottom five sheets is smaller than the difference between the top five and the bottom five. The impregnating liquid used in the measurement consists of 7% by weight of silicon resin particles having an average particle diameter of 2 μm, 1% by weight of silicon oil having a viscosity of 5 mm$^2$/sec at 25° C., 1% by weight of Carbopol, 15% by weight of ethanol, 0.5% by weight of ethyl p-hydroxybenzoate, and 75.5% by weight of water.

In order to obtain a base sheet having the above-defined preferred liquid migration resistance, it is one of conceivable methods that the base sheet is made up of a plurality of single-ply webs containing a sufficient amount of cellulosic fibers, such as pulp, for sufficiently retaining liquid. This method, however, sometimes has difficulty in securing a minimal peel strength between the webs as described later. To increase the peel strength, it is effective to use thermoplastic resin fiber in an increased population. The problem is this case is that most of thermoplastic resin fibers are generally hydrophobic and incapable of retaining the impregnating liquid sufficiently. Then the present inventors have found that the above-specified liquid migration characteristics can be obtained conveniently by the following method.

In using a single-ply web comprising cellulosic fiber and thermoplastic resin fiber and containing hydrophobic fiber in a high proportion, it is effective to interpose the web between single-ply webs having a larger proportion of cellulosic fiber than that web. In other words, it is effective to use two or more kinds of single-ply webs comprising cellulosic fiber and thermoplastic resin fiber in such a manner that a single-ply web having a smaller proportion of cellulosic fiber (i.e., a larger proportion of thermoplastic resin fiber) is sandwiched in between single-ply webs having a larger proportion of cellulosic fiber (i.e., a smaller proportion of thermoplastic resin fiber). According to this method it is considered that the above-defined liquid migration characteristics can be secured because the web having a high proportion of cellulosic fiber acts as a barrier layer for preventing liquid from moving down while exhibiting sufficient liquid retention, and also because the multi-ply structure affords ampler space in which liquid can be held.

In a preferred example, a first layer having an increased proportion of cellulosic fiber so as to retain sufficient liquid (e.g., comprising 80 to 99% of cellulosic fiber and 1 to 20% of thermoplastic resin fiber) and a second layer having a lower proportion of the cellulosic fiber and a higher proportion of the thermoplastic resin fiber than the first layer so as to exhibit improved peel strength (e.g., comprising 50 to 90% of the cellulosic fiber and 10 to 50% of the thermoplastic resin fiber) are superposed to prepare a two-ply composite sheet. Two two-ply composite sheets are superposed with their second layers facing each other to make a four-ply structure, which is then united into one body by a prescribed means, for example, heat sealing to complete a unitary base sheet having a multi-ply structure. The middle two plies (the second layers) comprising a larger amount of the thermoplastic resin fiber have excellent heat sealability. Besides, the thermoplastic resin fibers are thicker and more uniform in thickness than the cellulosic fibers to that they form spaces among themselves to make the whole sheet bulky and soft. Further, the outermost layers (the first layers) comprising a larger amount of the cellulosic fiber retain ample liquid and serves as a barrier layer preventing the liquid from migrating downward. Such an appropriate combination of two kinds of single webs provides a unitary base sheet that has various functions by itself. By having a multi-ply structure, a single base sheet has a sufficient thickness and feels soft and agreeable when used as a wet sheet.

The base sheet according to the present invention may have either a single-ply structure or, as described above, a multi-ply structure composed of two or more webs. Fibrous materials can constitute the sheet, including natural fibers, such as pulp and cotton, regenerated fibers, such as rayon and acetate, and fibers comprising thermoplastic resins, such as polyester, polyethylene, polypropylene, polyurethane, acrylic resins, and polyamide. Pulp is preferably used; for it provides the base sheet with a dense surface, making it easy to control the average pore diameter within the above-described specific range. Where the base sheet is impregnated with an aqueous medium, it is preferred to use hydrophilic fibers, such as cellulosic fiber, or hydrophobic fibers having been treated to have hydrophilicity. It is also preferred to use pulp and thermoplastic resin fiber in a prescribed ratio from the standpoint of improvement on the texture. Where two or more webs are bonded to make a multi-ply base sheet, such a combination is also preferred from the standpoint of improvement on the bonding strength. The thermoplastic resin fibers may be conjugate fibers or splitable fibers, etc. In using hydrophobic thermoplastic fibers in a major proportion, it is necessary to treat the fibers to make them hydrophilic in case where the base sheet is to be impregnated with an aqueous medium while supporting powder thereon. Such a treatment is unnecessary where the base sheet is used as a dry sheet containing no liquid. In using the thermoplastic resin fibers, it is particularly preferred to use fibers comprising polyethylene terephthalate (PET), polyethylene, polypropylene, and the like from the viewpoint of sheet strength. Bulkiness or gloss that is hardly obtainable by a sole use of cellulosic fiber such as pulp will be imparted to the base sheet by using thermoplastic resin fiber comprising an acrylic resin, polyamide, etc.

Where the base sheet has a multi-ply structure composed of two or more single-ply webs of the same or different kinds, bulkiness with a sufficient thickness is obtained, and with an impregnating aqueous medium the multi-ply base sheet provides a wiping sheet which is comfortable in wiping and exhibits sufficient liquid retention.

Where the base sheet has a multi-ply structure, it is preferred that the constituent single-ply webs be bonded together by a prescribed means into a unitary sheet as hereinafter described. It is preferred for the adjoining webs to have a peel strength of 50 cN/75 mm or more, particularly 100 cN/75 mm or more, especially 150 cN/75 mm or more. With this preferred peel strength, separation of layers is prevented effectively while the liquid-impregnated base sheet is used as a wiping sheet, and the ease and feel of use are improved. There is no particular upper limit of the peel strength. The higher the peel strength, the better for prevention of layer separation. With the texture and the like being taken into consideration, however, about 400 cN/75 mm would be a preferred upper limit.

The plurality of single-ply webs can be bonded by, for example, adhesion with a hot-melt adhesive or a double-sided adhesive tape, press bonding, and heat sealing. Where the base sheet is used as a wet sheet impregnated with an aqueous medium, heat sealing is a preferred means for securing a sufficient peel strength even while wet.

Adjacent single-ply webs are preferably bonded in parts so as to minimize impairment of the texture. A preferred bonding area is 3 to 50%, particularly 5 to 15%, of the entire area of the base sheet.

The peel strength of the multi-ply base sheet is measured as follows. A 100 mm long and 75 mm wide strip cut out of the base sheet is partly separated into two webs at one end to make a Y-shape. The separated ends are held by the chucks of a tensile tester having the distance between chucks set at 15 mm and pulled apart at a speed of 300 mm/min. The maximum stress of pulling is taken as a peel strength.

The single-ply webs making up the multi-ply base sheet may be the same or different in the composition of the above-described fibrous materials. From the standpoint of the texture of the whole sheet, the peel strength between the webs, and the liquid absorption capacity of the sheet, it is preferred to use single-ply webs comprising cellulosic fiber and thermoplastic resin fiber. For obtaining a base sheet with a dense surface and improved texture, a preferred weight ratio of the cellulosic fiber to the thermoplastic resin fiber ranges from 99:1 to 50:50, particularly 95:5 to 75:25. This ratio is also preferred for obtaining sufficient liquid retention and satisfactory heat sealability. Where the base sheet is a single-ply sheet, the whole sheet preferably has the above composition. Where the base sheet is a multi-ply sheet, at least the outermost ply preferably has the above composition.

Where the base sheet is composed of two or more single-ply webs, it is preferred that each single-ply web contains the thermoplastic resin fiber and that the adjacent plies be joined by partly pressing or fusion bonding the thermoplastic resin fibers to form discontinuous or continuous joint areas whereby the plies are made into a unitary sheet. For securing sufficient integrity, the press bonding or fusion bonding is preferably conducted until the joint areas come to be almost flat in a film form. An ordinary roll sealer or heat sealer is used to carry out press bonding or fusion bonding.

A particularly preferred embodiment of the base sheet is a four-ply base sheet prepared by superposing two single-ply webs comprising cellulosic fiber (e.g., pulp) and thermoplastic resin fiber which are different in composition (designated webs A and B), forming unevenness on the two-ply structure, superposing two two-ply structures with the webs of the same kind (i.e., webs A or webs B) facing each other, and joining the four webs into an integral sheet by partial press bonding or fusion bonding. In case where the base sheet is to be impregnated with an aqueous medium, it is still preferred that the facing two webs, i.e., the inner two webs, contain the thermoplastic resin fiber in a larger proportion than the outer two webs (i.e., the proportion of the cellulosic fiber in the facing inner two webs is lower than that in the outer two webs).

Where the single-ply web constituting the base sheet is made of a fibrous material, it may have the form of nonwoven fabric, paper, woven fabric, knitted fabric, etc. Nonwoven fabric or paper is preferred for controllability of the average pore diameter D, the bulk softness and the thickness, the proportion of fibers, fabricability, the production cost, and the like. The nonwoven fabric or paper is preferably prepared by a melt-blown method, a flash spinning method, a method comprising splitting conjugate fibers by a physical or chemical means and bonding or interlacing the split filaments by water needling, thermal fusion or resin bonding, or a dry or wet paper making method using pulp as a main component. These methods are advantageous for producing a dense sheet with a controlled average pore diameter within the above-described specific range. For obtaining a denser sheet, a wet paper making method using pulp as a main fibrous material is preferred.

It is a preferred embodiment to subject the resulting base sheet to general calendering for obtaining a dense sheet with a controlled average pore diameter within the above range. Calendering is particularly effective on nonwoven fabric of cotton or rayon fiber prepared by the water needling method. Calendering for making the sheet surface smooth is preferred for not only nonwoven fabric but other sheets such as woven fabric. Where a base sheet containing synthetic resin fiber is calendered while heating, it is preferable to reduce the mixing ratio of the synthetic resin fiber to prevent impairment of the texture.

The basis weight of the base sheet is not particularly limited and may be adjusted appropriately according to the end use of the wiping sheet. A general range of the basis weight is from about 10 to about 200 g/m².

Powder is supported on the base sheet to make a wiping sheet. The powder preferably has an average particle diameter d of 1 to 30 μm, particularly 1 to 15 μm, in relation to the average pore diameter D of the base sheet. The average particle diameter d of powder can be measured by a laser diffraction method or a centrifugation method. Powder whose average particle diameter is smaller than 1 μm shows little effect to the feel of the skin or tends to have an unpleasant squeaky feel. Powder having an average particle diameter exceeding 30 μm tends to have an unpleasant rough feel when applied to the skin. It is desirable for the powder to contain practically no coarse particles of 200 μm or greater.

From consideration of the feel to the skin and the economy, it is preferred that powder having an average particle diameter of 1 to 30 μm be supported in an amount of 0.05 to 60 g, particularly 0.26 to 40 g, per m² of the base sheet.

Powder can be supported on the base sheet by, for example, scattering the powder directly on the base sheet, soaking the base sheet in a dispersion of the powder in an aqueous medium, such as water or an aqueous alcohol, or spraying the powder to the base sheet by means of a spray or an air gun.

The wiping sheet having the powder supported thereon is preferably capable of transferring 40% or more, particularly 60% or more, of the powder to an object of wiping. If the rate of powder transfer is less than 40%, leaving 60% or more of the powder remaining on and in the base sheet, the effects of powder application are hardly exerted. The rate of powder transfer is measured as follows. A 150 mm long and 100 mm wide sample cut out of the wiping sheet is placed on the center of a sheet of black drawing paper whose weight has previously been measured (weight A). A double stroke of a pressure roller is given to the sample under a load of 0.44 kg/cm² at a speed of 5 cm/sec. The sample is removed, and the drawing paper is completely dried and weighed (weight B). Subtracting weight A from weight B gives the weight of transferred powder. The weight of the transferred powder is divided by the weight of the powder initially present on the sample, and the quotient is multiplied by 100 to give the rate of transfer (%) of the powder.

Additionally, for securing sufficient effects of powder application, the wiping sheet having powder preferably has such powder transfer properties as to make a color difference of 6 or more, particularly 8 to 30, on the black drawing paper between before and after the powder transfer in the above measurement. The color difference is measured with a differential colorimeter CR-210 (manufactured by Minolta) for the black drawing paper on which the powder has been transferred in the above measurement of weight B.

The powder to be supported on the base sheet is preferably spherical. While the sphericity of the powder is not so significant, it is preferred to use particles as close to true spheres as possible because the coefficient of dynamic friction decreases to improve the skin smoothness as the sphericity increases.

Any powders of synthetic polymers or natural minerals can be used. A powder of synthetic polymers is preferred in that it reduces the coefficient of dynamic friction when applied to the skin to impart a smooth feel to the skin.

Powders of synthetic polymers include fine polymer particles obtained by dispersion polymerization of a vinyl monomer in a solvent in the presence of a polysiloxane compound having a radical polymerizable group at one terminal thereof as a dispersant (hereinafter referred to as polymer beads S), and particles of silicone resins, nylon resins, polystyrene resins, polyethylene resins, polymethyl methacrylate resins, divinylbenzene resins, synthetic silica, polyurethane resins, benzoguanamine resins, melamine resins, phenol resins, and fluoropolymers. Preferred of them are polymer beads S, silicone resin particles, and polystyrene resin particles for their properties of reducing the frictional force on the skin, imparting a smooth feel to the skin, and staying on the skin.

Powders of natural minerals include particles of talc, sericite, mica, kaolin, red oxide, clay, bentonite, silicic acid, silicic anhydride, magnesium silicate, magnesium oxide, zinc oxide, titanium oxide, aluminum oxide, aluminum sulfate, alum, calcium sulfate, barium sulfate, and magnesium sulfate. Talc is preferred of them for its good slip on the skin.

Besides having powder supported, the base sheet is preferably impregnated with an aqueous medium to provide a wet wiping sheet for wiping an object or the skin. The aqueous medium which can be used is not particularly limited as long as it is fit for the purpose of wiping or cleaning. Water and aqueous alcohols can be used, for example. The base sheet is preferably impregnated with 50 to 500% by weight, particularly 100 to 400% by weight, of an aqueous medium based on its own weight for giving an improved feel of use. The alcohol preferably includes ethanol, propylene glycol, 1,3-butanediol, isoprene glycol, glycerol, and sorbitol. If desired, the aqueous medium may contain drugs having an antimicrobial effect or a moisture retaining effect.

When a wiping sheet comprising a pulp-containing base sheet impregnated with an aqueous medium is allowed to left in air, the aqueous medium evaporates, and the pulp in the base sheet is yellowed to deteriorate the appearance. To avoid this, it is a highly preferred embodiment to incorporate 0.5 to 5% by weight of polyethylene glycol to the aqueous medium. The present inventors analyzed the part of the wiping sheet comprising the pulp-containing base sheet impregnated with an aqueous medium which had locally dried and underwent yellowing. As a result, it was confirmed that the part contained 9.8% by weight of lignin. Generally speaking, an analysis of a bleached pulp sheet does not reveal the presence of lignin. It is conceivable that residual lignin remaining unbleached migrates to a specific part and concentrated to cause yellowing as the wiping sheet dries. It is also conceivable that mixed saccharide (disaccharides) derived from cellulose or hemicellulose remaining in the bleached pulp undergo denaturation due to aerial oxidation to generate a coloring group, which causes yellowing. Whatever causes the yellowing, the presence of polyethylene glycol suppresses or prevents yellowing even when some coloring substance causing yellowing moves to a part where the liquid content is decreasing due to drying and is concentrated there, probably because a sufficient liquid content is maintained in that part by virtue of containing polyethylene glycol thereby preventing contact of the coloring substance with oxygen in air. It could be possible that the base sheet is previously impregnated with polyethylene glycol prior to impregnation with an aqueous medium containing no polyethylene glycol. In this case, however, there is difficulty in controlling the impregnation with polyethylene glycol, and it is very likely that too much polyethylene glycol infiltrates the base sheet, resulting in an unpleasant sticky feel.

The concentration of polyethylene glycol in the aqueous medium is preferably 0.5 to 5% by weight, still preferably 0.5 to 3% by weight, particularly preferably 0.5 to 1% by weight. If the concentration is lower than 0.5% by weight, the effect in preventing yellowing may be insufficient. If it exceeds 5% by weight, the aqueous medium will have an increased viscosity, deteriorating the wiping performance, the convenience of use, and the feel to the touch. Incorporation of polyethylene glycol in the preferred concentration is effective in suppressing or preventing yellowing of pulp without adversely affecting the wiping performance or the convenience of using the wiping sheet. Since polyethylene glycol is of high safety for the human body and free from an unpleasant small, the wiping sheet containing it can be used at ease and without discomfort.

To ensure suppression or prevention of yellowing of pulp, it is preferred for the aqueous medium to contain 1.0 to 15.5 parts by weight, particularly 1.5 to 3.0 parts by weight, of polyethylene glycol per 100 parts by weight of pulp constituting the base sheet.

The polyethylene glycol to be added preferably has an average molecular weight of 300 to 600 to suppress or prevent pulp yellowing more effectively without impairing the wiping performance or the feed of use. The polyethylene glycol may contain other oxyalkylene groups, such as an oxypropylene group, to a degree not ruining the effects of the present invention.

To further improve the feel on wiping, it is another preferred embodiment to incorporate silicone oil having a viscosity of 1 to 200 mm$^2$/sec at 25° C. into the base sheet in an amount 1/100 to 10 times, particularly 1/50 to twice, as much as the powder. The silicone oil to be used preferably includes methylpolysiloxane and dimethylpolysiloxane.

Oily substances other than silicone oil which are liquid at ambient temperature may also be incorporated. The other oily substances which can be used to improve the feel of use include avocado oil, tsubaki oil, turtle oil, corn oil, olive oil, wheat germ oil, soybean oil, jojoba oil, peanut oil, cacao butter, lanolin, liquid paraffin, squalane, squalene, vaseline, and cholesteryl esters. The base sheet may also contain additives according to the use. For example, wiping sheets for personal care can contain physiologically effective moisturizing components, antiinflammatory agents, skin whitening agents, UV care agents, antimicrobial agents, anhidrotics, deodorants, fresheners, perfumes, and so forth.

When the wiping sheet having powder supported on the base sheet is used for wiping the skin, it clears dirt of the skin and at the same time efficiently apply the powder to the skin. The powder thus applied stays on the skin for a long time, making the skin feel smooth and fresh. The wiping sheet containing a moisturizing component, an antiinflammatory agent, a skin whitening agent, a UV care agent, an antimicrobial agent, an anhidrotic, a deodorant, a freshener, a perfume, etc. not only conditions the skin functionally but makes the user feel refreshed with moderate moisture and a pleasant scent. The wiping sheet is usually packaged in a closed container or bag to prevent liquid from evaporating and, on every use, taken out one by one.

The present invention is not construed as being limited to the above-mentioned embodiments of the practice. For example, the single-ply web made of a fibrous material can be replaced or combined with a film or a foamed sheet. When the base sheet is to be impregnated with an aqueous medium, the film or the foamed sheet can be rendered hydrophilic.

Where the base sheet has a multi-ply structure, the plurality of single-ply webs making up the multi-ply structure do not always need to be different. Even where the constituent single-ply webs are of the same kind, a multi-ply base sheet is apparently different from a single-ply sheet in texture, softness, thickness, and feel on use. Where the base sheet is made up of three or more single-ply webs, it is preferred that at least one interface of two adjacent webs has the above-described peel strength.

The present invention will now be illustrated in greater detail with reference to Examples. Unless otherwise noted, all the percents are given by weight.

EXAMPLES 1 TO 6 AND COMPARATIVE EXAMPLES 1 AND 2

A base sheet was impregnated with 275% of an impregnating liquid prepared as described later by spraying to prepare a wiping sheet. The average pore diameter D, bulk softness, thickness, amount of powder, peel strength, liquid migration, embossing, and heat sealing of the base sheet is shown in Table 1.

The polymer beads S used in the impregnating liquid were synthesized as follows.

Synthesis of Polymer Beads S:

A 500 ml four-necked flask equipped with a condenser, a thermometer and a stirrer was purged with nitrogen, and 275.9 g of n-hexane, 90 g of toluene, and 1.58 g of a polysiloxane compound having a methacryloxy group at one terminal thereof (Silaplain FM-0725, produced by Chisso Corp.; number average molecular weight: 10,000) were put therein and heated to 70° C. To the flask were added 39.50 g of methyl methacrylate 13.17 g of styrene, and 1.06 g of lauroyl peroxide (polymerization initiator), and the mixture was allowed to react at 70° C. for 12 hours. The reaction system was initially uniform, assumed a bluish white color in about 10 minutes from the addition of the initiator, and thereafter became a white emulsion. The reaction mixture was allowed to cool, diluted with 200 g of n-hexane, and centrifuged. The separated solid was re-dispersed in 300 g of n-hexane, followed by centrifugation. The washing with n-hexane and centrifugal separation were repeated once more. The solid was vacuum dried in a drier at 50° C. to give 54.0 g of a white powder. The resulting powder (polymer beads S) was found to be monodispersed particles having an average particle diameter d of 2 μm.

Of the base sheets shown in Table 1, pulp sheets A to D and rayon sheets A and B were prepared as follows.

Preparation of Base Sheets:

1) Pulp sheet A

A mixture of 90% of pulp (NBKP) and 10% of PET/low-melting PET core/sheath type conjugate fiber was beaten and, after removal of foreign matter, made into a web having a basis weight of 30 g/m$^2$ (designated web 1). The web 1 was subjected to matched steel roll embossing.

2) Pulp sheet B

A mixture of 80% of pulp (NBKP) and 20% of PET/low-melting PET core/sheath type conjugate fiber was beaten and, after removal of foreign matter, made into a web having a basis weight of 30 g/m$^2$ (designated web 2). The web 1 and web 2 were superposed and subjected to matched steel roll embossing. Two embossed two-ply sheets were superposed with the webs 2 facing each other and heat-sealed according to a prescribed pattern to obtain a four-ply sheet.

3) Pulp sheet C

Two webs 1 were superposed and subjected to matched steel roll embossing. Two embossed two-ply sheets were superposed and heat-sealed in the same manner as for pulp sheet B.

4) Pulp sheet D

Two webs 1 were superposed, subjected to matched steel roll embossing, and heat-sealed according to a prescribed pattern to obtain a two-ply sheet.

5) Rayon sheet A

A web made of a mixture of 70% of rayon and 30% of splitable filaments of PP/PE conjugate fibers was needled with water jets and calendered to obtain nonwoven fabric having a basis weight of 40 g/m$^2$. Two sheets of the nonwoven fabric were superposed and heat-sealed according to a prescribed pattern to obtain a two-ply rayon sheet.

6) Rayon sheet B

A web made of a mixture of 70% of rayon and 30% of PET fiber was needled with water jets to obtain nonwoven fabric having a basis weight of 40 g/m$^2$.

Preparation of Impregnating Liquid:

A mixture of 3% of polymer beads S (average particle diameter: 2 μm), 1% of silicone oil (viscosity at 25° C.: 5 mm$^2$/sec), 1% of Carbopol, 15% of ethanol, 0.5% of ethyl p-hydroxybenzoate, and 79.5% of water was mixed in a homomixer.

Evaluation on Performance:

The wiping sheets obtained in Examples 1 to 6 and Comparative Examples 1 and 2 were evaluated for the powder transfer properties including the rate of transfer and the color difference on black drawing paper in accordance with the previously described methods. The results obtained are shown in Table 1.

Five female users and five male users whose age were twenties to forties were asked to wipe all over their body with the wiping sheet and to rate the wiping sheet for the feel on and after use, including smoothness of the skin, roughening of the skin, and the wetness of the sheet, according to the following rating scales.

Skin smoothness after use:

A . . . smooth

B . . . slightly smooth

C . . . not smooth

Skin roughening after use:

A . . . causing no skin roughening

B . . . causing slight skin roughening

C . . . causing skin roughening

Wetness on use:

A . . . moderate

C1 . . . dry

C2 . . . wet

The numbers of test users who rated as "A (two points)", "B (one point)" or "C (zero point)" for each attribute and the average point of the attribute are shown in Table 1.

TABLE 1

|  |  | Example | | | | | | Comp. Example | |
|---|---|---|---|---|---|---|---|---|---|
|  |  | 1 | 2 | 3 | 4 | 5 | 6 | 1 | 2 |
| Base Sheet |  | pulp sheet A | pulp sheet B | pulp sheet C | cotton nonwoven | pulp sheet D | rayon sheet A | cotton mesh nonwoven | rayon sheet B |
| Average Pore Diameter D (μm) |  | 1.3 | 1.3 | 1.3 | 22 | 1.3 | 36 | 40 | 65 |
| D/d |  | 0.65 | 0.65 | 0.65 | 11 | 0.65 | 18 | 20 | 36 |
| Bulk Softness (N/30 mm) |  | 1.6 | 1.7 | 1.7 | 0.5 | 1.6 | 1.0 | 0.3 | 0.5 |
| Thickness (mm) |  | 0.95 | 1.6 | 1.7 | 0.4 | 0.95 | 0.9 | 0.25 | 0.45 |
| Embossing |  | done | done | done | undone | done | undone | undone | undone |
| Heat Sealing |  | undone | done | done | undone | done | done | undone | undone |
| Amount of Supported Powder (g/m$^2$) |  | 5 | 10 | 10 | 10 | 10 | 10 | 10 | 10 |
| Rate of Powder Transfer (%) |  | 75 | 85 | 85 | 60 | 85 | 50 | 20 | 25 |
| Color Difference |  | 17.0 | 18.5 | 18.5 | 11.0 | 18.5 | 9.5 | 2.0 | 5.0 |
| Smoothness | A | 7 | 8 | 8 | 7 | 8 | 6 | 1 | 0 |
|  | B | 2 | 1 | 1 | 2 | 1 | 3 | 8 | 7 |
|  | C | 1 | 1 | 1 | 1 | 1 | 1 | 1 | 3 |
|  | Avg. | 1.6 | 1.7 | 1.7 | 1.6 | 1.7 | 1.5 | 1.0 | 0.7 |
| Skin Roughening | A | 7 | 8 | 8 | 6 | 8 | 7 | 1 | 1 |
|  | B | 2 | 1 | 1 | 3 | 1 | 2 | 4 | 1 |
|  | C | 1 | 1 | 1 | 1 | 1 | 1 | 5 | 8 |
|  | Avg. | 1.6 | 1.7 | 1.7 | 1.5 | 1.7 | 1.6 | 0.6 | 0.3 |
| Wetness | A | 6 | 8 | 8 | 7 | 8 | 7 | 1 | 1 |
|  | C1 | 3 | 1 | 1 | 2 | 1 | 2 | 1 | 9 |
|  | C2 | 1 | 1 | 1 | 1 | 1 | 1 | 8 | 0 |
|  | Avg. | 1.2 | 1.6 | 1.6 | 1.4 | 1.6 | 1.4 | 0.2 | 0.2 |
| Peel Strength (cN/75 mm) | 1/2* |  | 113 | 100 |  | 135 | 220 |  |  |
|  | 2/3** |  | 210 | 162 |  |  |  |  |  |
|  | 3/4*** |  | 113 | 100 |  |  |  |  |  |
| Liquid migration (Liquid content Diff.; %) | Top 5 Layers | 268 | 270 | 267 | 261 | 267 | 273 | 262 | 268 |
|  | Bottom 5 Layers | 282 | 288 | 282 | 289 | 282 | 277 | 290 | 281 |

Note:

*1/2: Between 1st and 2nd layers

**2/3: Between 2nd and 3rd layers

***3/4: Between 3rd and 4th layers

As is apparent from the results in Table 1, the wiping sheets of Examples 1 to 6 are superior to those of Comparative Examples 1 and 2 in the feel of use, that is, they provide a smooth feel without causing skin roughening, and the comfortable feel lasted.

As described above, the present invention presents a base material for a wiping sheet which efficiently transfers powder supported thereon to an object of wiping. A wiping sheet comprising the base material of the present invention having powder supported thereon can be used for the skin to not only wipe the skin but efficiently apply the powder to the wiped skin. The applied powder makes the skin feel smoother, giving a user a new and unique refreshment.

Where, in particular, the base material has a multi-ply structure having a certain peel strength between plies, it is bulky with a sufficient thickness, feels good when used for wiping, does not twist while used, has softness and an excellent texture, and exhibits sufficient liquid retention.

Yellowing of the base material that might have occurred where the base material contains pulp can be prevented effectively by incorporating polyethylene glycol into the impregnating aqueous medium in a specific concentration.

This application claims the priority of Japanese Patent Application Nos. 11-96469 and 11-96470 each filed Apr. 2, 1999, which are incorporated herein by reference.

What is claimed is:

1. An uneven wiping sheet having pores and comprising an uneven base material on which powder is supported and in which an aqueous medium is impregnated, wherein the base material is impregnated with from 50 to 500% by weight of the aqueous medium and wherein the powder is supported on the surface or in the vicinity of the surface of the sheet and wherein the ratio of the average pore diameter (D) of the surface of said base material while dry as measured by the mercury penetration method to the average particle diameter (d) of said powder, D/d, ranges from 0.03 to 30, said base material while dry has a bulk softness of from 0.1 to 5 N/30 mm and a thickness of from 0.3 to 5 mm, said average pore diameter (D) ranges from 0.1 to 30 μm, said average particle diameter ranges from 1 to 30 μm, said base-material has a multi-ply structure comprising two or more single-ply webs of the same kind or different kinds, each web contains cellulosic fibers and thermoplastic resin fibers, and said thermoplastic resin fibers contained in adjacent plies of said webs are partially press bonded or fusion bonded to form a joint area wherein the uneven base material is formed by embossing using a matched pair of steel rolls wherein said cellulosic fiber comprises pulp, and said aqueous medium contains polyethylene glycol in a concentration of 0.5 to 5% by weight and wherein 40% or more of the supported powder is transferred to an object of wiping when the object is wiped with said wiping sheet.

2. The wiping sheet according to claim 1, wherein the peel strength between two adjacent plies is 50 cN/75 mm or greater.

3. The wiping sheet according to claim 1, which has such liquid retention properties that, when a stack of thirty wiping sheets of 150 mm in length and 100 mm in width each impregnated with 2.75 times its own weight of an impregnating liquid is allowed to stand for 24 hours, the difference in average liquid content (%) between the top five wiping sheets and the bottom five wiping sheets is 30% or less.

4. The wiping sheet according to claim 1, wherein one surface and the other surface of said wiping sheets having substantially the same performance in absorbing or releasing liquid, supporting powder, transferring the powder to an object, and/or wiping off.

5. The wiping sheet comprising the base material according to claim 1 having supported thereon 0.05 to 60 g/m$^2$ of powder having an average particle diameter of 1 to 30 μm, and having been impregnated with an aqueous medium.

6. A wiping sheet according to claim 5, which transfers said supported powder to black drawing paper in such an amount that makes a color difference of 6 or more when said supported powder is transferred from the wiping sheet to said black drawing paper.

7. The wiping sheet according to claim 1, wherein said base material has a multi-ply structure comprising single-ply webs, each web contains cellulosic fibers and thermoplastic resin fibers, wherein the multi-ply structure is comprised of a web having a smaller proportion of cellulosic fiber that is sandwiched in between webs having a larger proportion of cellulosic fiber.

8. The wiping sheet according to claim 7, wherein said base sheet is a four-ply structure prepared by superposing two single-ply webs comprising cellulosic fibers and thermoplastic resin fibers which are different in composition, forming unevenness on the two-ply structure, superposing two two-ply structures with the webs of the same kind facing each other, and joining the four webs into an integral sheet by partial press bonding or fusion bonding, the facing two inner webs contain said thermoplastic resin fibers in a larger proportion than the outer two webs.

9. A wiping sheet according to claim 5, wherein said cellulosic fiber comprises pulp, and said aqueous medium contains 1.0 to 15.5 parts by weight of polyethylene glycol per 100 parts by weight of pulp constituting said base sheet.

* * * * *